United States Patent [19]

Warriner

[11] Plant 5,246

[45] Jun. 19, 1984

[54] ROSE PLANT—JACIBE

[75] Inventor: William A. Warriner, Tustin, Calif.

[73] Assignee: Jackson & Perkins Company, Medford, Oreg.

[21] Appl. No.: 428,315

[22] Filed: Sep. 29, 1982

[51] Int. Cl.[3] ..... A01H 5/00

[52] U.S. Cl. ..... Plt./7

[58] Field of Search ..... Plt./5, 7

*Primary Examiner*—Robert E. Bagwill

*Attorney, Agent, or Firm*—Klarquist, Sparkman, Campbell, Leigh & Whinston

[57] ABSTRACT

A miniature rose variety having compact, upright plant habit; orange-red flower color on upper side of petals with lighter shade on reverse; short, pointed bud; rigid petals; and mild fragrance.

1 Drawing Figure

1

This present invention relates to a new and distinct variety of rose plant of the miniature class which was originated by me by crossing the variety Bridal Pink, U.S. Plant Pat. No. 2,851, with the variety Fire Princess, U.S. Plant Pat. No. 3,084.

The primary objective of this breeding was to produce a new rose variety combining the miniature habit of growth of the pollen parent, petal texture of pollen parent, flower form of seed parent, and color between the two parents. This objective was substantially achieved along with other desirable improvements as evidenced by the following unique combination of characteristics which are outstanding in the new variety and which distinguish it from its parents, as well as from all other varieties of which I am aware:

1. Compact, upright plant habit, reaching less than 3 feet at maturity.
2. Flower color of orange-red (RHS 34C) on upper side of petals, lighter on reverse.
3. Short pointed bud.
4. Rigid petals causing flower form to last well.
5. Mild resistance to mildew.
6. Very mild fragrance.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated.

Parentage:

*Seed parent.*—Bridal Pink, U.S. Plant Pat. No. 2,851.

*Pollen parent.*—Fire Princess, U.S. Plant Pat. No. 3,084.

Classification:

*Botanical.*—Rosa hybrid.

*Commercial.*—Miniature.

2

FLOWER

Observations made from specimens grown at Irvine, Calif., in July, 1982.

Blooming habit: Continuous.

Bud:

*Size.*—$\frac{5}{8}''$ to $\frac{3}{4}''$ when petals start to unfurl.

*Form.*—Short, pointed.

*Color.*—When sepals first divide, near Orange-Red 34C with large near white area at base of petals. When half blown; upper side of petals near Orange-Red 34C with large, clearly defined area near petal base of near white, lower side of petals slightly lighter than Orange-Red 34C with white basal area not clearly defined.

*Sepals.*—Color: outer surface Green 138A heavily overlaid with Greyed Purple 184A. Surface contains numerous stipitate glands. Three appendaged sepals normally appendaged. Two unappendaged sepals hairy edged.

*Receptacle.*—Color: Green 138A, heavily overlaid with Greyed Purple 184A. Shape: funnel. Size: large. Surface: slightly hairy.

*Peduncle.*—Length: short. Surface: slightly glandular. Color: bronzy. Strength: stiff, erect.

*Opening.*—Petals fold out, slightly curling.

Bloom:

*Size.*—Small. Average open size is $1\frac{3}{4}''$ to $2''$.

*Borne.*—In clusters, flat.

*Stems.*—Short, strong.

*Form.*—When first open, high center. Permanence: retains its form to the end; outer petal edges slightly curled.

*Petalage.*—Number of petals under normal conditions: 45–50.

*Color.*—Center of flower: upper side of petals near Orange-Red 34C with large white basal area clearly defined; reverse side of petals lighter than Orange-Red 34C with large white basal area not clearly defined; base of petals white. General tonality from a distance Orange-Red 34C.

*Variegations.*—Occasional white streak in center of petal.

*Discoloration.*—General tonality at end of first day: no change. Third day: very little change.

*Fragrance.*—Slight.

Petals:

*Texture.*—Thin, but quite rigid.

*Shape.*—Nearly round, but slightly wider than long.
*Form.*—Edges slightly quilled.
*Arrangement.*—Imbricated. Petaloids in center: few.
*Persistence.*—Drop off cleanly.
*Lastingness.*—On the plant, very long. As cut flower, very long.

Reproductive parts:
*Anthers.*—Large. Color: dull yellow. Arrangement: regular around styles.
*Filaments.*—Color: white.
*Pollen.*—Gold yellow.
*Styles.*—Color: light reddish.
*Stigmas.*—Color: white.

PLANT

Form: Bush.
Growth: Vigorous, dwarf, growing to under 3 feet.
Foliage: Number of leaflets on normal mid-stem leaves: 5 or 7.
*Size.*—Medium.
*Quantity.*—Abundant.
*Color.*—New foliage: Green 138A, overlaid heavily with Greyed Purple 187C. Old foliage: Green 137A.

Leaflets:

*Shape.*—Elliptic.
*Texture.*—Upper side: leathery.
*Edge.*—Serrated.
*Serration.*—Single, small.
*Petiole.*—Rachis: color: reddish. Underside: few prickles.
*Stipules.*—Long.
*Disease resistance.*—Slightly susceptible to mildew under normal growing conditions at Irvine, Calif.

Wood:
*New wood.*—Color: light green. Bark: smooth.
*Old wood.*—Color: green. Bark: smooth.

Prickles:
*Quantity.*—On main stalks from base, many. On laterals from stalk, many.
*Form.*—Long, hooked downward.
*Color when young.*—Brown.
*Position.*—Irregular.

I claim:

1. A new and distinct variety of rose plant of the miniature class, substantially as herein shown and described, characterized particularly as to novelty by the unique combination of its compact plant, pointed, orange-red buds and flowers and mild fragrance.

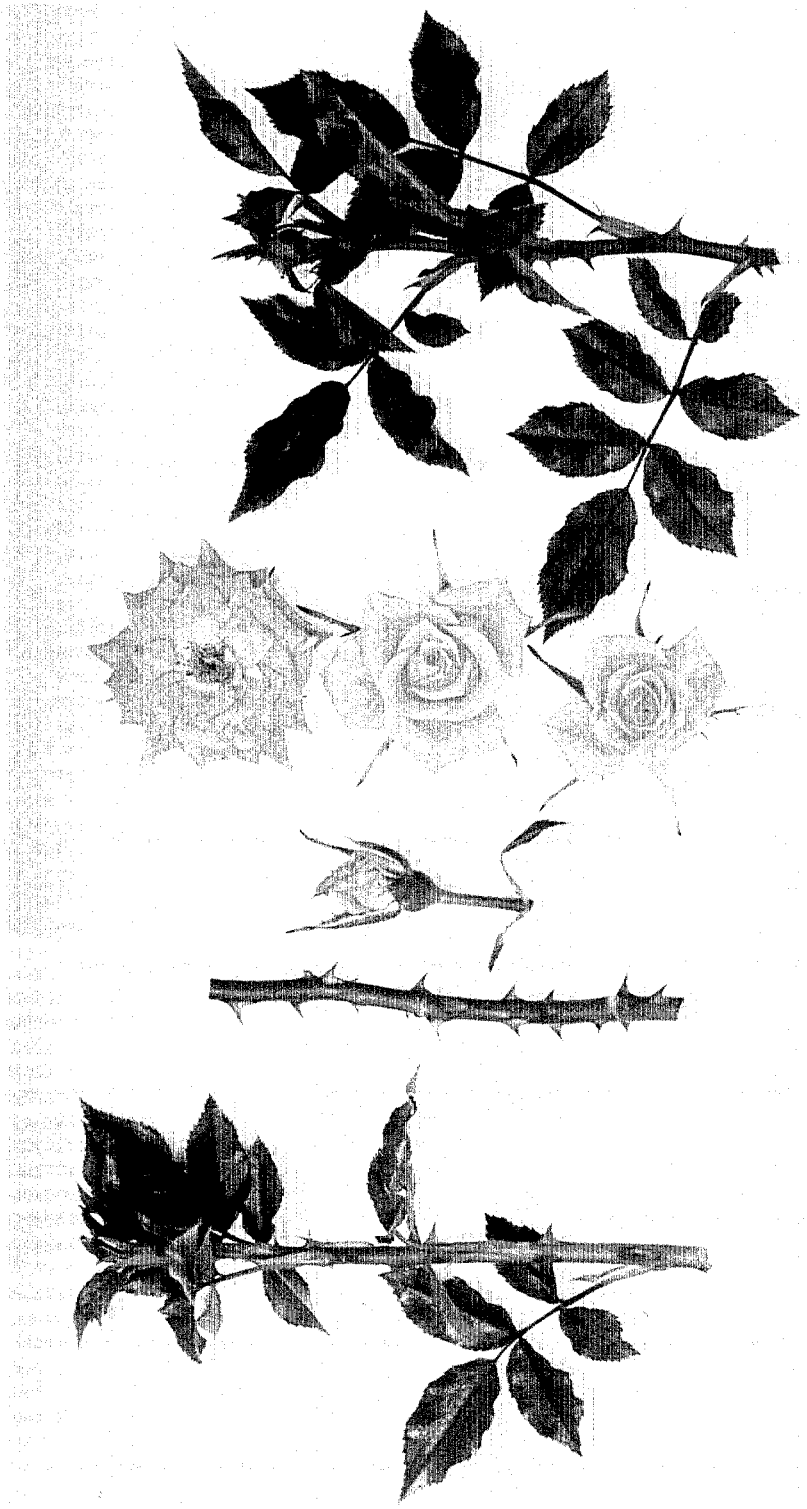

* * * * *